(12) United States Patent
Akimoto et al.

(10) Patent No.: US 7,822,262 B2
(45) Date of Patent: Oct. 26, 2010

(54) OUTER SURFACE-INSPECTING METHOD, MASTER PATTERNS USED THEREFOR, AND OUTER SURFACE-INSPECTING APPARATUS EQUIPPED WITH SUCH A MASTER PATTERN

(75) Inventors: Shigeyuki Akimoto, Kawagoe (JP); Takashi Itoh, Saitama (JP)

(73) Assignee: Kabushiki Kaisha TOPCON, Itabashi-ku, Tokyo (JP)

(*) Notice: Subject to any disclaimer, the term of this patent is extended or adjusted under 35 U.S.C. 154(b) by 201 days.

(21) Appl. No.: 10/556,916

(22) PCT Filed: May 17, 2004

(86) PCT No.: PCT/JP2004/006622

§ 371 (c)(1),
(2), (4) Date: Nov. 15, 2005

(87) PCT Pub. No.: WO2004/102171

PCT Pub. Date: Nov. 25, 2004

(65) Prior Publication Data

US 2007/0053579 A1        Mar. 8, 2007

(30) Foreign Application Priority Data

May 16, 2003    (JP)    ............... 2003-139344

(51) Int. Cl.
G06K 9/00        (2006.01)
(52) U.S. Cl. ...................... 382/149; 382/199
(58) Field of Classification Search ............... 382/149, 382/145, 181
See application file for complete search history.

(56) References Cited

U.S. PATENT DOCUMENTS 4,479,145 A * 10/1984 Azuma et al. ............... 382/199

(Continued)

FOREIGN PATENT DOCUMENTS

EP        0 643 293        3/1995

(Continued)

OTHER PUBLICATIONS

European Search Report issued in corresponding European Patent Application No. 04 73 3426, dated Jan. 15, 2008.

*Primary Examiner*—Vu Le
*Assistant Examiner*—Michael Vanchy, Jr.
(74) *Attorney, Agent, or Firm*—Buchanan Ingersoll & Rooney PC

(57) ABSTRACT

The invention is to provide an outer surface-inspecting method, a master pattern and an outer surface-inspecting apparatus, which can eliminate severe positional alignment of the master pattern, avoid erroneous judgment taking acceptable products as unacceptable ones and suppress increase in number of standard pattern portions to be prepared as a master pattern. In the method and the apparatus, an outer surface of inspection areas 16a to 16i having repeated patterns are inspected through comparison with the predetermined master pattern. The inspection area is divided into a plurality of matrix-like view areas 16a to 16i. Mutually different standard pattern portions 17a to 17i are used depending upon different edge shapes of the divided inspection areas 16a to 16i contained in the inspection area, respectively. The present invention is suitable for inspecting the outer surface of a semiconductor chip such as a memory or a CCD (charge-coupled device).

3 Claims, 4 Drawing Sheets

U.S. PATENT DOCUMENTS

| | | | | |
|---|---|---|---|---|
| 4,532,650 A * | 7/1985 | Wihl et al. | | 382/144 |
| 4,680,627 A | 7/1987 | Sase et al. | | |
| 5,023,917 A * | 6/1991 | Bose et al. | | 382/149 |
| 5,513,275 A * | 4/1996 | Khalaj et al. | | 382/149 |
| 5,608,816 A * | 3/1997 | Kawahara et al. | | 382/149 |
| 5,764,793 A * | 6/1998 | Omae et al. | | 382/149 |
| 5,774,574 A * | 6/1998 | Hoki | | 382/149 |
| 6,171,737 B1 * | 1/2001 | Phan et al. | | 430/30 |
| 6,504,947 B1 * | 1/2003 | Nozaki et al. | | 382/148 |
| 6,701,004 B1 * | 3/2004 | Shykind et al. | | 382/149 |
| 6,760,473 B1 * | 7/2004 | Fiekowsky | | 382/149 |
| 6,913,861 B2 * | 7/2005 | Shishido et al. | | 430/30 |
| 6,952,492 B2 * | 10/2005 | Tanaka et al. | | 382/149 |
| 6,959,112 B1 * | 10/2005 | Wagman | | 382/181 |
| 2002/0149765 A1 | 10/2002 | Fujii et al. | | |
| 2004/0023128 A1 * | 2/2004 | Yamamoto et al. | | 430/5 |

FOREIGN PATENT DOCUMENTS

| | | |
|---|---|---|
| EP | 643293 A1 * | 3/1995 |
| GB | 2 190 743 | 11/1987 |
| JP | 60-123709 | 7/1985 |
| JP | 61-047635 A | 3/1986 |
| JP | 2002-109515 A | 4/2002 |

* cited by examiner

OUTER SURFACE-INSPECTING METHOD, MASTER PATTERNS USED THEREFOR, AND OUTER SURFACE-INSPECTING APPARATUS EQUIPPED WITH SUCH A MASTER PATTERN

TECHNICAL FIELD

The present invention relates to outer surface-inspecting apparatus and method suitable for inspecting the outer surfaces of semiconductor chips such as memories or CCD (charge coupled elements) having repeating patterns thereon.

BACKGROUND ART

According to one conventional inspection method for judging whether a semiconductor chip has a defect or not, a pattern matching method is available in which a master pattern obtained from a good-quality product is compared with an image pattern obtained from the outer surface of the semiconductor chip as an object to be inspected (For example, see Patent Literature 1).

According to this method, the comparison of both the patterns makes it possible that a defect liable to cause insufficiently electric contact, such as dust attached to the semiconductor chip or scratch of bump or the like, can be detected by image data processing, so that whether the semiconductor is good or not can be effectively judged.

Patent Literature 1: JP-A 2002-109515 (Pages 3 and 4, FIG. 2)

DISCLOSURE OF THE INVENTION

Problems to Be Solved by the Invention

Among the semiconductor chips to be inspected, a number of identical structural portions are formed in an arrayed fashion on a substrate of the semiconductor chip. In such a semiconductor chip, a fundamental pattern having the identical structure is repeated on the outer surface of such a semiconductor chip.

Therefore, it is considered in the inspection of the outer surface of the semiconductor chip having such repeating patterns that a single standard pattern portion which is in conformity with a standard pattern being the repeating pattern unit is used as a master pattern and that this standard pattern portion is compared with each of the image portion corresponding to areas of the semiconductor chip to be inspected.

However, when the single standard pattern portion is used and the standard pattern portion is applied to a corner portion as an edge portion of the rectangular inspection area, for example, the standard pattern portion needs to be aligned with the image of the inspection area severely based on the data so that the standard pattern portion may not run out of the area to be inspected. If the standard pattern portion runs over the edge of the view area to be inspected in this aligning step, matching is not made between the standard pattern portion and the image on the area to be inspected at the run-over portion. Consequently, the object to be inspected is judged to be unacceptable.

Under the circumstances, the present invention is aimed at providing a outer surface-inspecting method, a master pattern and a outer surface-inspecting apparatus and having repeated patterns by comparing a predetermined master pattern, the outer surface-inspecting method making it unnecessary to make severe positional alignment of the master pattern, avoiding erroneous judgment taking acceptable products as unacceptable ones and suppressing increase in number of standard pattern portions, and said master pattern and the outer surface-inspecting apparatus being used for the outer surface-inspecting method.

Measures for solving the Problems

In order to accomplish the above objects, the outer surface-inspecting method according to the present invention for inspecting the outer surface of the inspection area having repeated patterns through comparing a predetermined master pattern is characterized in that said inspection area is divided into a plurality of matrix-like view areas, mutually different standard pattern portions are used as a master pattern for respective different edge shapes of said inspection area contained in said divided view areas, said standard pattern portions involving said respective edge portions, and the outer surface of the inspection area are inspected by comparing the standard pattern portions to the view areas corresponding to the standard pattern portions.

The master pattern according to the present invention is a master patter to be used for comparison with an outer surface of an inspection area having repeated patterns for the purpose of inspecting said inspection area, characterized in that said master pattern comprises a plurality of mutually different standard pattern portions for respectively different edge shapes of said inspection area contained in a plurality of matrix-like view areas, said view areas being obtained by dividing said inspection area, wherein the outer surface of the inspection area is to be inspected by comparing the standard pattern portions to the outer surfaces of the view areas corresponding to the respective standard pattern portions.

The outer surface-inspecting apparatus used to inspect an outer surface of an inspection area having repeated patterns according to the present invention is characterized in that said outer surface-inspecting apparatus comprises a master pattern, said master pattern comprising a plurality of mutually different standard pattern portions for respectively different edge shapes of said inspection area contained in a plurality of matrix-like view areas, said view areas being obtained by dividing said inspection area, wherein the outer surface of the inspection area is to be inspected by comparing the standard pattern portions to the outer surfaces of the view areas corresponding to the respective standard pattern portions.

According to the outer surface-inspecting method and the outer surface-inspecting apparatus of the present invention, the standard pattern portion having the same edge shape is used as a master pattern for each side portion showing the same edge shape at the peripheral edge portion of the inspection area. Since the standard pattern portions are used corresponding to the respective edge shapes of the inspection areas, different standard patterns need not be prepared for the divided inspection view areas, respectively. Thus, the outer surface can effectively inspected, by the standard pattern portions in a number smaller than that of the view areas, without needing such severe alignment as to prevent the erroneous judgment, therefore without causing the erroneous judgment.

When the inspection area is rectangular, it is divided into the view areas by dividing the rectangular inspection area in horizontal and vertical directions. In this case, said standard pattern portions can be constituted by at least two kind of corner pattern portions each to be applied to corner portions of the inspection area and involving such edges of the inspection area as defining a corner portion, and at least one kind of side pattern portion to be applied between the corner portions of the inspection area and containing a part of an edge between the edge portions.

In general, the corner pattern portions may comprise four kinds of corner pattern portions to be applied to four corners of the inspection area, respectively, and said side pattern portion may comprise four kinds of side pattern portions to be applied along four sides of the inspection area, respectively. The standard pattern portions may further comprise one kind of a central pattern portion not containing an edge of the inspection area. Thereby, said standard pattern portions may comprise totally nine kinds of the standard pattern portions in the case of the rectangular inspection area.

When the master pattern is constituted by such totally nine kinds of the standard patterns, the outer surface can be effectively performed by preparing the nine kinds of the standard pattern portions at the maximum irrespective of the size of the inspection area and irrespective of the case where the inspection area is enlarged as the magnification rate of the inspection area is increased, for example.

The outer surface-inspecting method and apparatus can be applied to semiconductor chips having repeated patterns like memories and CCD, and various objects to be inspected having repeated patterns of a few microns to tens microns.

BEST MODE OF THE INVENTION

Figure 1:
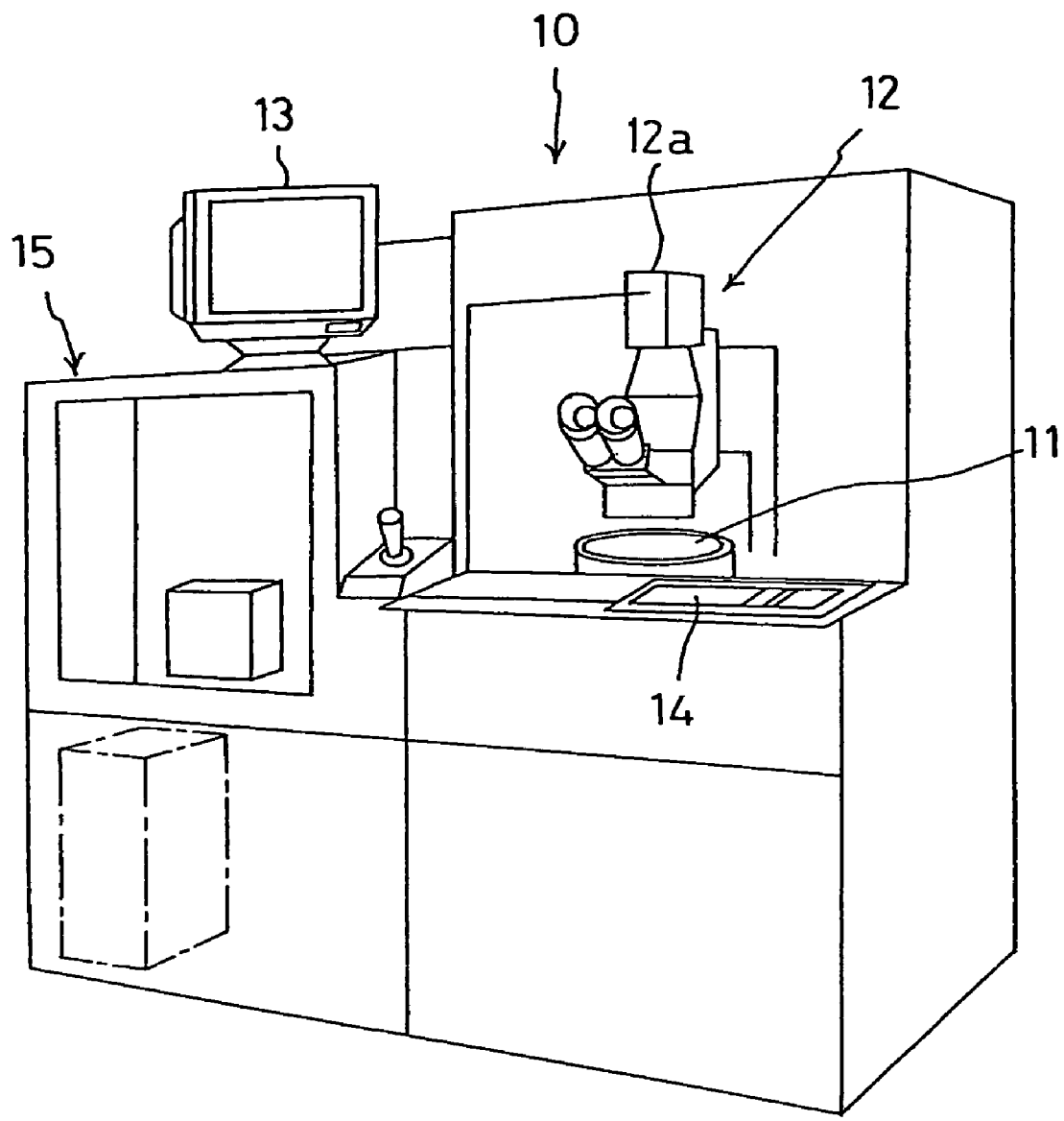
FIG. 1 is a perspective view schematically showing an outer surface-inspecting apparatus for carrying out an outer surface-inspecting method according to the present invention.

FIG. 1 schematically shows an embodiment of an outer surface-inspecting apparatus for carrying out the outer surface-inspecting method according to the present invention. The outer surface-inspecting apparatus shown in FIG. 1 is applied to the inspection of an outer surface of a semiconductor chip such as a memory or a CCD.

As shown in FIG. 1, the outer surface-inspecting apparatus 10 according to the present invention comprises a sample stage 11, an imaging device 12, a monitor 13 and an operating plate 14. On the sample stage 11, a semiconductor wafer as a collective body of semiconductor chips to be inspected is arranged. The imaging device 12 has an observation optical system and an imaging unit 12a such as a CCD, for example. The observation optical system is to obtain images of the outer surfaces of a number of the semiconductor chips formed within the semiconductor wafer on the sample stage. The monitor 13 is to monitor the image obtained by the imaging device. As well known conventionally, the sample stage 11 is movable in X-Y directions and its inclination angle θ is also adjustable by manipulating an operation unit provided on the operation plate 14.

After the semiconductor wafer is placed onto the sample stage 11 from a wafer transfer device 15, the operation plate 14 is so manipulated that a desired semiconductor chip 16 formed inside the semiconductor wafer on the sample stage (See FIG. 2) may be imaged with the imaging device 12. The outer surface image of the semiconductor chip 16 obtained by the imaging unit 12a of the imaging device 12 is observable in the monitor 13.

As conventionally well known, the outer surface-inspecting apparatus 10 contains well-known image processor and arithmetic processor not shown, which are adapted to determine differences in image between an image pattern taken with the imaging device 12 and a master pattern through comparison of their data. Whether presence or absence of any defect of the object to be inspected, any foreign matter or the like is judged by operating the image processor and the arithmetic processor. The presence or absence of the foreign matter on the semiconductor chip is inspected based on the judgment result.

Embodiment 1

Figure 2:
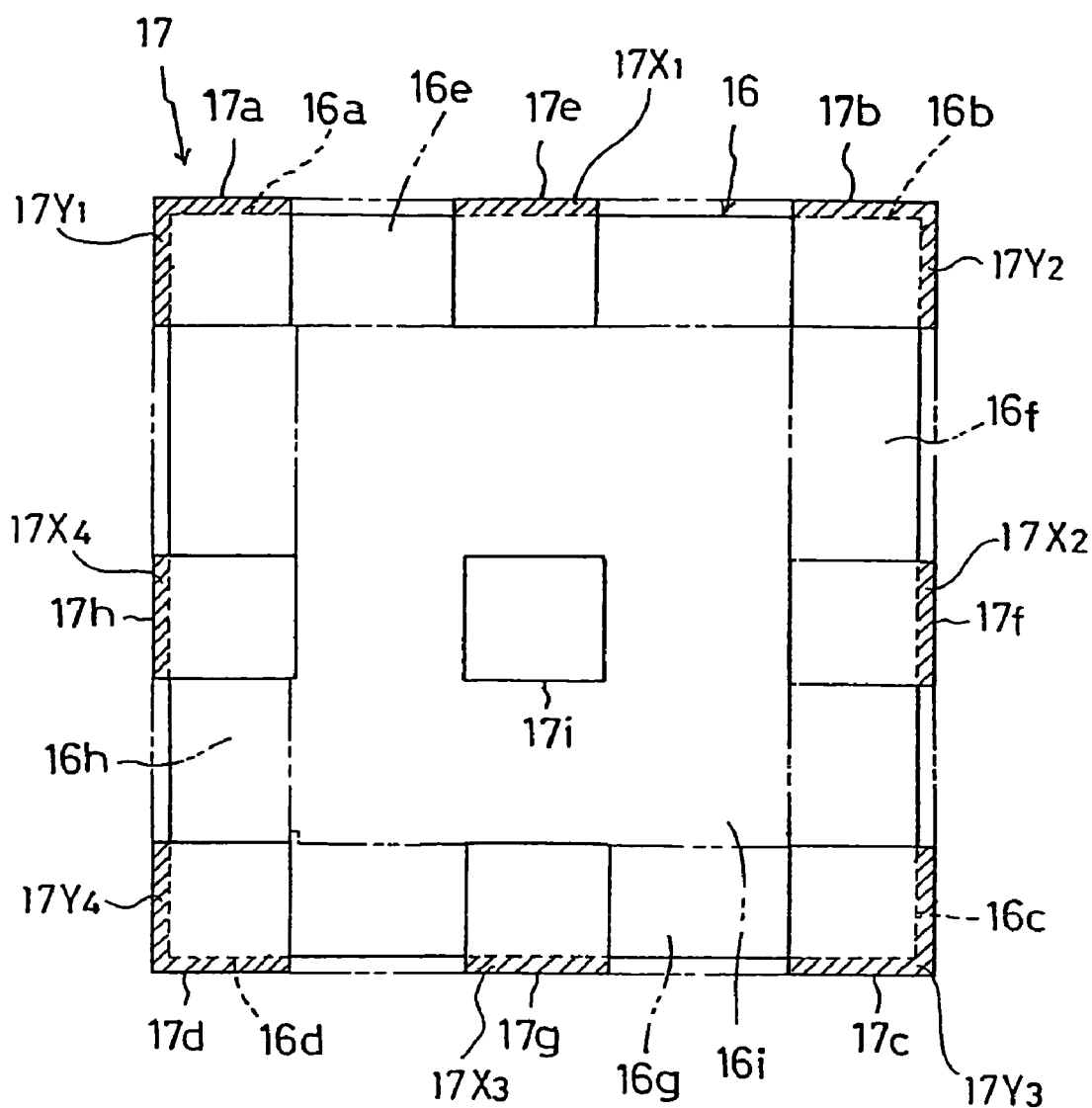
FIG. 2 gives relations between rectangular inspection areas and standard pattern portions constituting a master pattern in Embodiment 1 of the present invention as well as kinds of the standard pattern portions.

FIG. 2 shows correspondence between a master patterns 17 (17a to 17i) to be applied to the outer surface-inspecting apparatus 10 for performing the outer surface-inspecting method of the present invention and the semiconductor chip 16 to be inspected.

The semiconductor chip 16 has a rectangular planar shape which is taken as an area to be inspected (inspection area). The semiconductor chip 16 has identical patterns over the entire chip areas 16a to 16i to be inspected. The semiconductor chip 16 may be a memory or a CCD.

The inspection areas 16a to 16i of the semiconductor chip 16 are divided into a plurality of laterally and vertical view areas to be inspected (inspection view area) in a checkered pattern.

The master pattern 17 to be used for the inspection of the semiconductor chip 16 consists of totally nine kinds of standard pattern portions 17a to 17i: four kinds of corner pattern portions 17a to 17d to be applied to the four corner portions 16a to 16d of the semiconductor chip 16, respectively, four kinds of side pattern portions 17e to 17h to be applied to peripheral portions 16e to 16h involving four sides of the semiconductor chip 16, respectively, and one kind of a central pattern portion 17i to be applied to a central portion 16i surrounded by the corner portions 16a to 16d and the peripheral portions 16e to 16h. Each of the standard pattern portions 17a to 17i has a size almost corresponding to each of the inspection view areas, which are formed by the divided inspection areas 16a to 16i.

As seen in FIG. 2, the first corner pattern portion 17a is applied to the first corner portion 16a as the inspection view area, which is located at a left upper portion of the semiconductor chip 16, and the second corner pattern 17b, the third corner portion 16c and the fourth corner pattern portion 17d are applied clockwise successively to the inspection view areas of the second corner portion 16b, the third corner portion 16c and the fourth corner portion 16d, respectively.

It may be considered that a single corner pattern portion is used instead of the four corner pattern portions. However, such causes erroneous judgment due to warp aberration or the like in the observing optical system of the imaging device 12. In order to assuredly prevent such erroneous judgment based on the warp aberration or the like, the first to fourth corner pattern portions 17a to 17d are used for the four corner portions 16a to 16d, respectively so that the corner pattern portions 17a to 17d may be used for matching with the images of the corner portions 16a to 16d, respectively. Each of the corner pattern portions 17a to 17d comprises two perpendicular edges defining the respectively one of the corner portions 16a to 16d of the semiconductor chip 16 and a L-shaped outer area surrounding the edge portion of the semiconductor chip 16.

As shown in FIG. 2, the side pattern portions 17e to 17h are applied to edges of the semiconductor chip 16: the first side pattern portion 17e to be applied to a peripheral portion 16e along the upper side, i.e., a lateral edge of the semiconductor chip 16, the second side pattern 17f to be applied to the peripheral portion 16f along the right vertical side, i.e., a vertical edge of the semiconductor chip 16, the third side pattern 17g to be applied to the peripheral portion 16g along the lower side, i.e., a lateral edge of the semiconductor chip 16, and the fourth side pattern 17h to be applied to the vertically left portion 16h along the vertically left vertical side, i.e., a vertical edge of the semiconductor chip 16.

The side pattern portions 17e to 17h comprise straight edge portions $17X_1$ to $17X_4$ and outer edge portions $17Y_1$ to $17Y_4$ of the straight edge portions, respectively. The straight edge portions $17X_1$ to $17X_4$ define the vertical and lateral edges of the semiconductor chip 16, respectively.

The first side pattern portion 17e is moved, relative to each of the inspection view areas, along with the peripheral portion 16e between the first corner pattern portion 17a and the second corner pattern portion 17b, so that the first side pattern portion 17e is used for matching with each of the inspection view areas around the peripheral portion 16e. Similarly, the second side pattern portion 17f is moved, relative to each of the inspection view areas, along with the peripheral portion 16f between the second corner pattern portion 17b and the third corner pattern portion 17c, so that the second side pattern portion 17f is used for matching with each of the inspection view areas of the peripheral portion 16f. The third side pattern portion 17g is moved, relative to each of the inspection view areas, along with the peripheral portion 16g between the third corner pattern portion 17c and the fourth corner pattern portion 17d, so that the third side pattern portion 17g is used for matching with each of the inspection view areas around the peripheral portion 16g. The fourth side pattern portion 17h is moved, relative to each of the inspection view areas, along with the peripheral portion 16h between the fourth corner pattern portion 17d and the first corner pattern portion 17a, so that the fourth side pattern portion 17h is used for matching with each of the inspection view areas of the peripheral portion 16h.

The single central pattern portion 17i, which does not contain the edge portions of the semiconductor chip 16, is applied to every inspection view area in the central portion 16i of the semiconductor chip 16 surrounded by the peripheral portions 16e to 16h.

According to the outer surface-inspecting method of the present invention, the inspection area of the semiconductor chip 16 is divided into a plurality of lateral and vertical inspection view areas, and the standard pattern portions are classified according to the edge shapes of the semiconductor chip 16 contained in each inspection view area.

That is, in the embodiment 1 illustrated along with FIG. 2, the master pattern 17 is classified into the four corner pattern portions 17a to 17d having the L-shaped edge shape, the four side pattern portions 17e to 17h having the straight edge shape and the single master pattern 17h having no edge shape according to the different edge shapes of the semiconductor chip 16. The entire inspection view areas of the semiconductor chip 16 can be matched with these nine kinds of the standard pattern portions 17a to 17i, respectively by applying the standard pattern portions to the respective inspection view areas.

Each of these standard pattern portions 17a to 17h are to be applied to the four corner portions 16a to 16d and the four peripheral portions 16e to 16h, respectively, excluding the central portion 16i of the semiconductor chip 16, and contain the edge-shaped portions of the semiconductor chip 16, respectively, so that the standard pattern portions 17a to 17h contain the exterior area information depending upon the edge shape. Therefore, when the standard pattern portions 17a to 17h are to be matched with the corresponding inspection view areas, respectively, except for the central pattern portion 17i, a larger allowable error can be ensured as compared with the allowable error recognized in alignment with use of the standard pattern portion such as the central portion 17i containing no exterior area information.

That is, assume that the standard pattern portion not containing information on the edge shape or its exterior out area of the semiconductor chip 16 is to be positionally aligned with the corner portion 16a of the semiconductor chip 16, for example. Since this standard patter portion contains no exterior area information, the image data of the inspection area information largely differs from that of the standard pattern portion if the standard pattern portion is even slightly deviated outwardly from the semiconductor chip 16. Because, the image information in the exterior area caused by this deviation is taken in. To the contrary, according to the present invention of this application, since the information on the edge shapes and the exterior areas are correspondingly contained in the standard pattern portions 17a to 17h on the peripheral portion excluding the central pattern portion 17i, no severe positional alignment needs not be done unlike in the prior art. Therefore, the peripheral standard pattern portions 17a to 17h can be positionally aligned at a relatively large allowable error, that is, with the same allowable error as in the case of the central pattern portion 17i, so that erroneous judgment due to the error in this alignment is avoided. As a result, the occurrence of the erroneous judgment due to the error in arrangement of the standard pattern portion 17a to 17h constituting the master pattern 17 is avoided, and the effective surface inspection can be performed.

Embodiment 2

Figure 3:
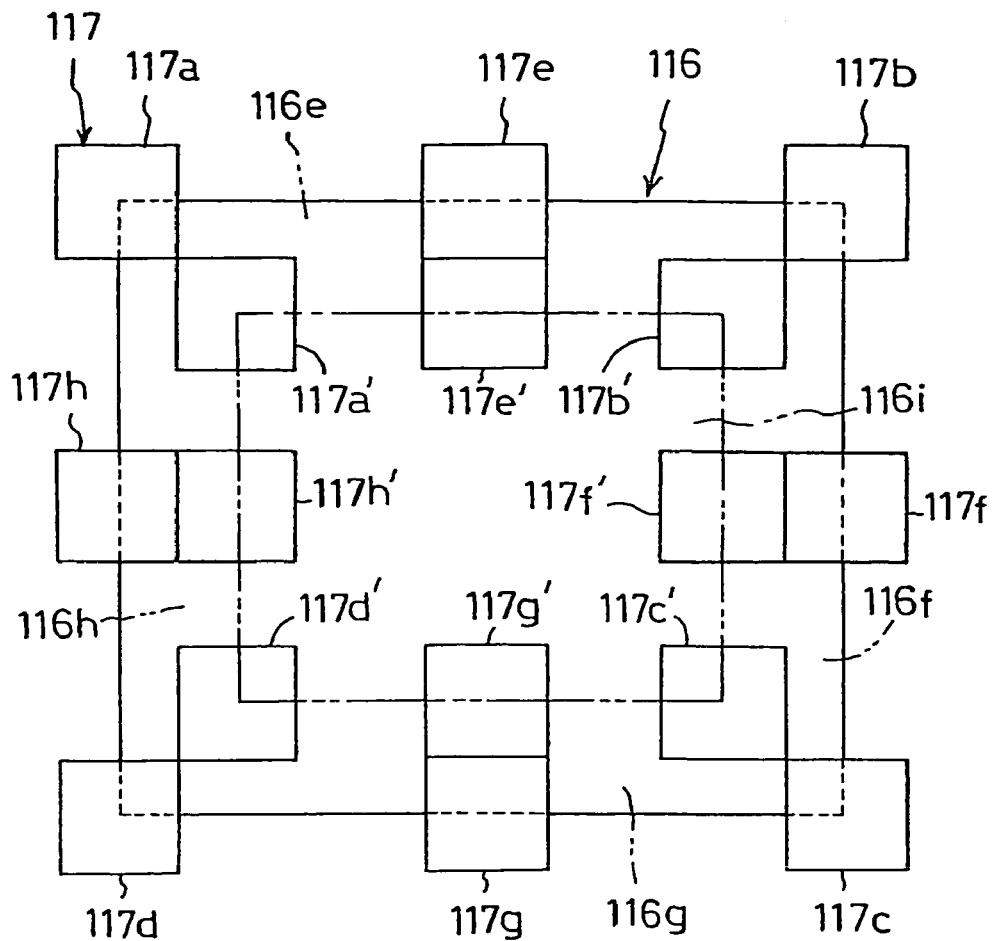
FIG. 3 is a view similar to FIG. 2 with respect to Embodiment 2 of the present invention.

FIG. 3 shows an example in which each of inspection areas is of a rectangular shape. Rectangular frame portions 116e to 116h are formed surrounding the rectangular central portion 116i of the semiconductor chip 116 to be inspected. The frame areas 116e to 116h have repeated patterns.

In this embodiment 2, a master pattern 117 is constituted by totally sixteen kinds of standard pattern portions: corner pattern portions 117a to 117d and side pattern portions 117e to 117h containing outer edges of frame areas 116e and 116h, respectively, corner pattern portions 117a' to 117d' containing inner edge portions of the frame areas 116e to 116h, respectively, and side pattern portions 117e' to 117h'.

The first to fourth side pattern portions are applied to the outer edges of the frame inspection areas 116a to 116h, respectively. That is, the first side pattern portion 117e is applied between the first corner pattern portion 117a and the second corner pattern portion 117b. The side pattern portion 117f is applied between the second corner pattern portion 117b and the third corner pattern portion 117c. The third side pattern portion 117g is applied between the third corner pattern portion 117c and the fourth pattern portion 117d. The fourth side pattern portion is applied between the fourth corner pattern portion 117d and the first pattern portion 117a.

The first to fourth corner pattern portions 117e' to 117h' are applied to the inner edges of the frame areas 116e to 116h, respectively. That is, the first side pattern portion 117e' is applied between the first corner pattern portion 117a' and the second corner pattern portion 117b', and the second side pattern portion 117f' is applied between the second corner pattern portion 117b' and third corner pattern portion 117c'. The third side pattern portion 117g' is applied between the third corner pattern portion 117c' and the fourth corner patter portion 17h', whereas the fourth corner pattern 117h' is applied between the fourth corner pattern portion 117d' and the first corner unit 117a'.

When sixteen kinds of the standard pattern potions 117a to 177h and 117a' to 117h' are used in such a frame-like inspection area, the erroneous judgment due to the erroneous arrangement of the standard pattern portions 117a to 117h and 117a' to 117h' constituting the master pattern 117 can be prevented to effectively inspect the outer surface.

If the central portion 116i has repeated patterns, the master pattern 17 shown in the first Embodiment 1 may be applied to the inspection of the outer surface of the pattern area 116i having the repeated patterns.

Embodiment 3

Figure 4:
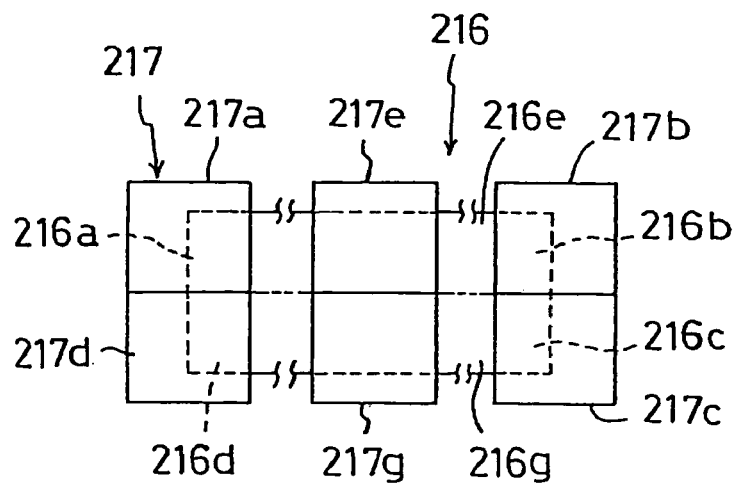
FIG. 4 is a view similar to FIG. 2 with respect to Embodiment 3 of the present invention.

FIG. 4 shows the inspection of repeated patterns of a semiconductor chip 216 having a narrower width as compared with Embodiment 1 and 2. A master pattern 217 is constituted by totally six kinds of standard pattern portions 217a to 217d, 217e and 217g: first to fourth corner pattern portions 217a to 217d, and the first and second side pattern portions 217e and 217g applied between first and second corner pattern portions 217a and 217b and between the third and fourth corner pattern portions 217c and 217d, respectively. The first to fourth corner pattern portions 217a to 217d are applied to the first to fourth corner portions 216a to 216d as the inspection view areas of the semiconductor chip 216, respectively. The first and second side pattern portions 217e and 217g are applied to the first and second intermediate portions 216e and 216g as the inspection view areas of the semiconductor chip 216, respectively.

Embodiment 4

Figure 5:
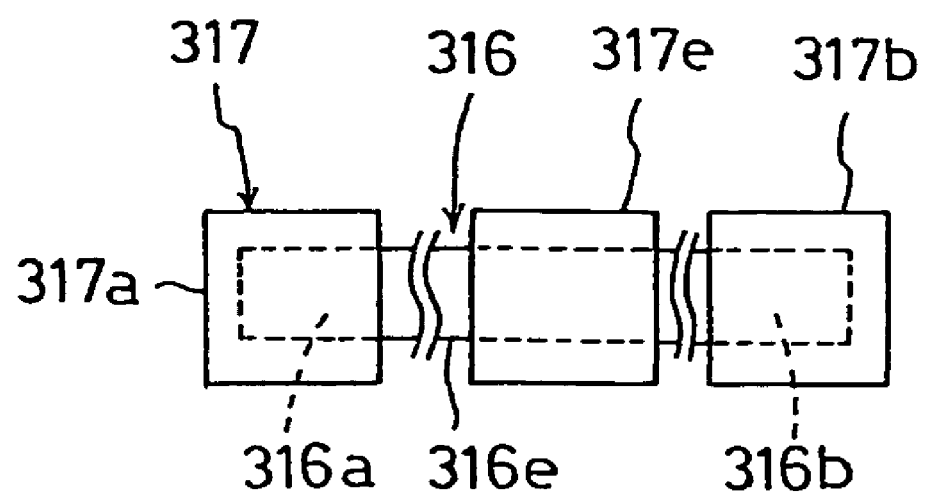
FIG. 5 is a view similar to FIG. 2 with respect to Embodiment 4 of the present invention.

FIG. 5 shows the inspection of the outer surface of repeated patterns of a semiconductor chips 316 having a further narrower width. A master pattern 317 can be constituted by totally three kinds of standard pattern portions: a first corner pattern portion 317a applied to an inspection view area 316a located at one end of the semiconductor chip 316 and containing a pair of corner portions, a second corner pattern portion 317b applied to an inspection view area 316b located at the other end of the semiconductor chip 316 and containing a pair of corner portions, and a single side pattern portion 317e including a pair of upper and lower edge portions of the semiconductor chip 316.

According to the present invention, since the standard pattern portions are used corresponding to the respective edge shapes of the inspection areas, different standard patterns need not be prepared for the divided inspection view areas, respectively. Thus, the outer surface can effectively inspected, by the standard pattern portions in a number smaller than that of the view areas, without needing such severe alignment as to prevent the erroneous judgment, therefore without causing the erroneous judgment.

INDUSTRIAL APPLICABILITY

The present invention can be used to inspect the outer surface of the semiconductor chip such as the memory or the CCD (charge-coupled device) having the repeated patterns thereon. Thus, the invention can be industrially used in the relevant technical field.

What is claimed is:

1. An outer surface-inspecting method using an outer surface inspecting apparatus for inspecting an outer surface of an inspection area having repeated patterns through comparison with a predetermined master pattern, said method comprising:

dividing said inspection area having a rectangular shape into a plurality of matrix-like view areas;

classifying a master pattern, according to respective different edge shapes of said inspection area, into nine standard pattern portions involving four corner pattern portions each of which is applied to a respective corner portion of the inspection area and has two perpendicular edges defining the respective corner portion and an L-shaped outer area surrounding the perpendicular edges, four side pattern portions each of which is applied to a respective side of the inspection area and has a straight edge portion defining a vertical edge or a horizontal edge and an outer edge portion of the straight edge portion, and a central pattern portion without having an edge portion of the inspection area;

moving each of the side pattern portions relative to the inspection view areas along a peripheral portion of the inspection area having the repeated patterns between respective corner pattern portions, so as to be applied to respective matching inspection view areas of the peripheral portion;

applying the single central pattern portion to matching of each of the inspection view areas at a central portion for the central portion surrounded by each of the peripheral portions; and inspecting the outer surface of the inspection area by comparing the standard pattern portions to the view areas corresponding to the classified standard pattern portions.

2. The outer surface-inspecting method set forth in claim 1, wherein an object to be inspected is a semiconductor chip.

3. An outer surface-inspecting apparatus used to inspect an outer surface of an inspection area having repeated patterns, said outer surface-inspecting apparatus comprising a master pattern, said master pattern comprising nine standard pattern portions involving four corner pattern portions each of which applied to a respective corner portion of the inspection area and has two perpendicular edges defining the respective corner portion and an L-shaped outer area surrounding the perpendicular edges, four side pattern portions each of which is applied to a respective side of the inspection area and has a straight edge portion defining a vertical edge or a horizontal edge and an outer edge portion of the straight edge portion, and one central pattern portion without having an edge portion of the inspection area, according to different edge shapes of said inspection area having a rectangular shape contained in a plurality of matrix-like view areas, said view areas being obtained by dividing said inspection area, wherein the outer surface of the inspection area is to be inspected by comparing the standard pattern portions to the outer surfaces of the view areas corresponding to the respective standard pattern portions.

* * * * *